United States Patent [19]

Debat et al.

[11] 4,263,285

[45] Apr. 21, 1981

[54] GLOBULARIA EXTRACT, ITS METHOD OF PREPARATION AND ITS USE AS PHARMACEUTICAL

[75] Inventors: Jacques Debat, Saint Cloud; Jean Lemoine, Garches; Monique Longuet, Auteuil le Roi, all of France

[73] Assignee: Societe Anonyme dite: Laboratoire Debat, Paris, France

[21] Appl. No.: 43,816

[22] Filed: May 30, 1979

[30] Foreign Application Priority Data

May 31, 1979 [GB] United Kingdom ............... 25619/79

[51] Int. Cl.³ .............................................. A01N 9/02
[52] U.S. Cl. .................................................. 424/195
[58] Field of Search ......................................... 424/195

[56] References Cited

PUBLICATIONS

Chem. Abstracts, vol. 82, (1975), Pars. 164,725j relied on.

Primary Examiner—Elbert L. Roberts
Attorney, Agent, or Firm—Stevens, Davis, Miller & Mosher

[57] ABSTRACT

This invention relates to an extract of a Globularia genus plant such as *Globularia alypum, Globularia vulgaris* and related species of the Globulariaceae family, which is useful as antibrucella, bacteriostatic and antiphlogistic agent.

This extract is obtained from the entire plant or a part of said plant by means of two extraction solvents of differing polarity.

This extract is useful in human and veterinary therapy, in particular in the treatment of brucellosis.

8 Claims, No Drawings

GLOBULARIA EXTRACT, ITS METHOD OF PREPARATION AND ITS USE AS PHARMACEUTICAL

BACKGROUND OF THE INVENTION AND PRIOR ART

*Globularia alypum* is a plant of the Globulariaceae family which grows in the Mediterranean basin. It has been described by HEGNAUER in "Chemotaxonomie der Pflanzen" vol. 4, pages 207-210 (1966) as well as *Globularia vulgaris* and related species of said Globulariaceae family.

In the past *Globularia alypum* was used or proposed in folk medicine for quite a lot of diseases. In particular water infusions of *Globularia alypum* flowers have been proposed as laxative, diuretic and antibrucella agents, and extracts of leaves have been proposed in the treatment of rhumatism, gout, typhoid, intermittent fever, as urinary antiseptic and as laxative.

More recently it has been disclosed by G. CALDES et al., in Planta Medica 27, 72-76 (1975) that extracts obtained from the entire plant of *Globularia alypum* by extraction with cold and boiling water then lyophilisation were (i) inactive as bacteriostatic (against *Staphylococcus aureus* and *Streptococcus faecium*) and antimalarial (against *Plasmodium berghi*) agents, and (ii) active against lymphocytic leukemia and neoplastic cell culture.

Taking into account the numerous and too different uses of *Globularia alypum* which have been proposed in the past, further studies have been carried out. These studies have now led to a new method of extraction of *Globularia alypum, Globularia vulgaris* and relates species of the Globulariaceae family, which surprisingly gives an extract which (i) is far more active as antibrucella agent than the previously known extracts, (ii) exhibits a bacteriostatic activity against Gram (+) bacteriae such as *Staphylococcus aureus*, and (iii) is also useful as antiphlogistic agent.

SUBJECT OF THE INVENTION

The subject of the invention is to propose a new method of extraction of a plant belonging to the Globularia genus such as *Globularia alypum, Globularia vulgaris* and relates species of the Globulariaceae family, in order to obtain a new extract which is useful in therapy, in particular in the treatment of human beings and mammiferous animals suffering from brucellosis, a disease which is also known as Malta fever.

DETAILED DESCRIPTION OF THE INVENTION

According to the present invention, the entire plant (that is to say the stems, the leaves, the floral apices, the fruit and the roots) or a part of the plant, such as for instance the stems, the leaves and the leavy stems (i.e. the stems and the leaves), is treated with two extraction solvents of differing polarity.

More precisely the method of preparation of an extract of Globularia useful in human and veterinary therapy, in particular in the treatment of brucellosis comprises the following steps:

(a) subjecting 10 to 120 g of a ground dried plant material of the Globularia genus chosen from the group comprising *Globularia alypum, Globularia vulgaris* and related species of the Globulariaceae family, to a first extraction with 1 liter of a solvent selected from the group consisting of water, alcohols, ketones, ethers, esters, hydrocarbons, halogenated hydrocarbons and mixtures thereof.

(b) discarding the insoluble material by filtration and subjecting the filtrate to a treatment selected from evaporation to dryness under reduced pressure, nebulisation and lyophilisation;

(c) subjecting the dry product thus obtained, to a second extraction with a solvent differing from the extraction solvent of step (a) by its polarity, and selected from the group consisting of water-alcohol mixtures, alcohols, ketones, methylene chloride, chloroform and mixtures thereof;

(c) discarding the insoluble material by filtration and evaporating the filtrate to dryness under reduced pressure; and, if necessary (e) subjecting the dry product of obtained according to step (d) to a purification which comprises a molecular filtration by chromatography with a support which relatively adsorbs rather the lower molecular weight substances than the higher molecular weight substances, in order to recover a fraction in which said higher molecular weight substances are predominant.

The extraction of step (a) can be carried out by using per liter of solvent, 10 to 120 g of ground and dried (at 37° C. in an oven) plant material.

The preferred plant material is the entire plant, the stems, the leaves or the leafy stems (i.e. the stems plus the leaves), the most interesting ones being the stems and the leaves.

Among the solvents of step (a) which can be used, it is possible to mention in particular water, alcohols (such as methanol, ethanol, propanol, isopropanol), ketones (such as acetone, methyl ethyl ketone, methyl propyl ketone), ethers such as dimethylether, diethyl ether, diisopropyl ether, esters (such as ethyl acetate), hydrocarbons (such as pentane, hexane, cyclopentane, cyclohexane, petroleum ether, benzene), halogenated hydrocarbons (such as chloroform, methylene chloride) and mixtures thereof.

The object of step (b) is to obtain a dry product from the filtrate. Lyophilisation and nebulisation (i.e. drying by projection) are used when the previous extraction of step (a) has been carried out with water. Evaporation to dryness under reduced pressure is used when the solvent of step (a) is an organic solvent, or a water-organic solvent mixture. Evaporation under reduced pressure then lyophilisation or nebulisation can also be used successively when the solvent of step (a) is a mixture of water with an organic solvent.

The extraction of step (c) is carried out by using preferably 50 to 300 ml of solvent per gram of product (b) to be treated.

In step (d) a relatively important amount of insoluble material which is non active as antibrucella, is discarded. In a general manner, when the solvent of step (c) is less polar then the one of step (a) it enables to discard from about 15 to 35% by dry weight of insoluble material with respect to the dry product (b) to be treated.

Step (e) is preferably carried out by using as eluent water, alcohols which are miscible with water, acetone or mixtures thereof. The chromatographic support can be either a nonionic resin or an ionic resin.

The best mode for carrying out the method of preparation according to the invention consists in (a) extracting 10 to 120 g of ground and dried stems and leaves ("leavy stems") of *Globularia alypum* with 1 liter of a solvent selected from the group consisting of water, alcohols, and mixtures thereof (the preferred solvent being distilled water), under reflux for 15 minutes to 5 hours;

(b) discarding the insoluble material by filtration and subjecting the solution thus obtained to a lyophilisation;

(c) subjecting the lyophilised product thus obtained to an extraction at room temperature (15°–25° C.) for 2 to 4 hours with methanol, a water-methanol mixture, ethanol and a water-ethanol mixture (the most intersecting solvent being here methanol), by using 50 to 300 ml of solvent per gram of lyophilised product to be treated, and more preferably by using 90 to 110 ml of solvent per gram of lyophilised product;

(d) discarding the insoluble material by filtration and evaporating the solution to dryness under reduced pressure; and (e) dissolving the evaporation residue thus obtained into a solvent preferably selected from water, methanol, ethanol and mixtures thereof, and subjecting the resulting solution to a column chromatography on a support suitable for molecular filtration.

The preferred support of step (e) is a non-ionic support which is commercialized under the name of Sephadex GH-20. The active fraction which contains in a predominant manner the relatively higher molecular weight substances is obtained first. If 10 volumes of solvent is used in step (e), three fractions are obtained successively; the first 3 volumes constitute Fraction I (which contains the active substances), the 3 volumes which follow constitute Fraction II (which is less interesting in therapy than Fraction I). The 3 last volumes obtained constitute Fraction III (which is also less interesting than Fraction I). Accordingly, when 1 to 5 g of evaporation residue are treated with 1 liter of solvent, the first 300 ml recovered at the bottom of the column constitute Fraction I, the whole time for obtaining the three Fractions being comprised between 6 and 9 hours (i.e. 2-3 for each fraction).

If needed Fraction I thus obtained can be evaporated to dryness under reduced pressure or lyophilised.

Thin layer chromatography shows that Fraction I mainly contains two stains of Rf 0.3 and 0.54 (see examples 1 and 2 hereinafter).

The following examples illustrate the invention.

EXAMPLE 1

*Globularia alypum* extract (A) Obtention of total extract 50 g of the whole plant of *Globularia alypum* dried in an oven at 37° C. and ground are extracted with 1.5 liters of water under reflux for 4 hours. The insoluble material is discarded by filtration and the aqueous solution is then lyophilised to give 10.2 g of a total extract. Yield: 20.5% by weight with respect to the starting plant material.

(B) Obtention of Fractions I, II and III 10 g of the total extract are treated for 2 hours at room temperature (15°–25° C.) with 1 liter of a water-ethanol (20:80) v/v mixture. The insoluble material (2 g) is discarded by filtration and the solution which is obtained is evaporated to dryness under reduced pressure to give 8 g of a dry product.

5 g of the dry product thus obtained have been treated according to the following operating conditions by means of an ion exchange resin:

column: diameter of 3 cm support: 120 ml of an ion exchange resin of the XAD-2 type deposit: 5 g of total extract dissolved in 20 ml of distilled water eluent: 980 ml of distilled water (total amount of water: 1 liter)

The first 300 ml recovered at the bottom of the column are lyophilised to give Fraction I; the next 300 ml are lyophilised to give Fraction II; the third 300 ml obtained at the bottom of the column are also lyophilised to give Fraction III.

Fraction I, the therapeutically active product, which is less adsorbed than the two other fractions, contains the major part of the higher molecular weight substances present in the dry product which was chromatographied.

Thin layer chromatography [support: cellulose; mobile phase: Partridge's upper phase, butanol-acetic acid—water (4:1:5) v/v/v developer: vanillin-sulphuric acid (1 g of vanillin per 100 ml of concentrated $H_2SO_4$ of density 1.84)] of Fraction I gives two main stains: one stain of Rf 0.3 (brown-red) and a second stain of Rf 0.54 (blue).

EXAMPLE 2

*Globularia alypum* extract (A) Obtention of total extract 100 g of leavy stems of *Globularia alypum* dried in an oven at 37° C. and ground are extracted with 4 liters of distilled water under reflux for 30 minutes. After cooling the insoluble material is discarded by filtration and the filtrate is then lyophilised to give 42 g of a total extract. Yield 42% with respect to the starting plant material.

(B) Obtention of Fractions I, II and III 3.3 of the total extract are treated at room temperature (15°–25° C.), with 300 ml of methanol for 3 hours. The insoluble material is discarded by filtration, and the solution thus obtained is evaporated to dryness under reduced pressure to give 2.21 g of a dry product.

2 g of said dry product in solution in 1 liter of methanol have subjected to a column chromatography (molecular filtration) with a column having a diameter of 3 cm and fed with a non ionic support (120 ml of Sephadex GH-20). The first 300 ml recovered at the bottom of the column are evaporated to dryness under reduced pressure to give Fraction I; the next 300 ml give, after evaporation to dryness under reduced pressure, Fraction II; the third 300 ml are evaporated under the same conditions to give Fraction III.

The yields with respect to the dry product which was chromatographied are as follows:

Fraction I: 3.7% by weight

Fraction II: 69.0% by weight

Fraction III: 15.7% by weight

As indicated in example 1B, Fraction I, with respect to Fractions II and III, contains the major part of the higher molecular weight substances.

Thin layer chromatography of Fraction I according to the method disclosed in example 1B gives the very same main stains of Rf 0.3 and Rf 0.54.

EXAMPLE 3

*Globularia vulgaris* extract

Stems of *Globularia vulgaris* extracted according to the method disclosed in example 2, with the difference that the total extract is obtained by treatment with 4 liters of a water-ethanol (85:15) v/v mixture then evaporation of $C_2H_5OH$ and lyophilisation, give Fractions I, II and III, Fraction I being the therapeutically active product.

The results of the pharmacological assays are summed up hereinafter.

(1°) Antibrucella activity

The antibrucella activity of Fractions I, II and III has been compared to the one of the corresponding total extracts taken as reference products, against several Brucella strains (the strain numbers being those of the catalogue of the collection of the "Service de Diagnostic des Brucelloses de l'Institut de Biologie" of Montpellier). The MIC (minimum inhibiting concentration) values, determined according to the dilution method in liquid medium, are given in table I.

(2°) Bacteriostatic activity

Fractions I of example 1 and example 2 inhibit gram (+) bacteriae such as cocci germs, while the corresponding total extracts are inactive. In particular the MIC values against *Staphylococcus aureus* London, determined according to the dilution method on solid medium (gelose), are as follows:

Fraction I of example 1: 2.50 mg/ml
Fraction I of example 2: 1.25 mg/ml (3°) Antiphlogistic activity Fractions I of examples 1-2 are most active than aspirin as antiphlogistic agents.

The invention includes within its scope a therapeutic composition comprising, in association with a physiologically acceptable excipient, a pharmaceutically effective amount of an extract of the invention.

Such a composition can be administered orally in the form of tablets, syrups and potable ampoules, or by injection.

TABLE I

| | | MIC VALUES (in µg/ml) | | | | | | |
|---|---|---|---|---|---|---|---|---|
| | | Example 1 | | | | Example 2 | | |
| Brucella strains | | Total Extract | Fraction I | Fraction II | Fraction III | Total Extract | Fraction I | Fraction II | Fraction III |
| *Brucella melitensis* type 1 | No 389 | >1000 | 100 | >2000 | 1000 | 1000 | 100 | >2000 | 1000 |
| | No 595 | 2000 | 250 | >2000 | 1000 | 2000 | 100 | >2000 | 1000 |
| | No 605 | >2000 | 250 | >2000 | 1000 | >2000 | 250 | >2000 | 1000 |
| | No 16M | >2000 | 100 | >2000 | >2000 | >2000 | 100 | >2000 | >2000 |
| *Brucella melitensis* type 2 | No 15 | >2000 | 250 | — | >2000 | >2000 | 100 | — | >2000 |
| | No 418 | 1000 | 4 | >2000 | >2000 | 1000 | 3.5 | >2000 | >2000 |
| | No 473 | 2000 | 100 | >2000 | 1000 | 2000 | 250 | >2000 | 1000 |
| | No 546 | >2000 | 7.2 | >2000 | >2000 | 2000 | 7.5 | >2000 | 1000 |
| *Brucella abortus* | No 19 | >2000 | 250 | >2000 | >2000 | >2000 | 250 | >2000 | >2000 |
| | No 112 | >2000 | 250 | — | >2000 | >2000 | 500 | >2000 | >2000 |
| | No 544 | 500 | 3.5 | >2000 | 1000 | 500 | 2.5 | >2000 | 1000 |

What is claimed is:

1. A method of preparation of an extract of Globularia which is useful in human and veterinary therapy which comprises the steps of:
   (a) extracting 10 to 120 g of a ground dried plant of Globularia alypum, Globularia vulgaris or related species of the Globulariaceae family, under reflux for 15 minutes to 5 hours with 1 liter of a solvent selected from the group consisting of water, alcohols, ketones, ethers, esters, hydrocarbons, halogenated hydrocarbons and mixtures thereof;
   (b) filtering the resulting extract and subjecting the filtrate to evaporation to dryness under reduced pressure, nebulisation or lyophilisation;
   (c) subjecting the resulting product thus obtained, to a second extraction at 15°-25° C. for 2 to 4 hours with a solvent differing from the extraction solvent of step (a) by its polarity, and selected from the group consisting of water-alcohol mixtures, alcohols, ketones, methylene chloride, chloroform and mixtures thereof in a ratio of 50 to 300 ml solvent per gram of said resulting product;
   (d) filtering the resulting extract and evaporating the resulting filtrate to dryness under reduced pressure.

2. A method according to claim 1 in which the plant material is the entire plant.

3. A method according to claim 1 in which the plant material is selected from the group comprising the stems, the leaves, the leavy stems, the floral apices, the fruit and the roots.

4. A method according to claim 3 in which the plant material consists of stems and leaves.

5. A method according to claim 1 in which the extraction of step (a) is carried out with a solvent selected from water, methanol, ethanol, and mixtures thereof.

6. A method according to claim 1 in which the extraction of step (c) is carried out with a solvent selected from methanol, ethanol and their mixtures with water, at room temperature for 2-4 hours, by using 50 to 300 ml of solvent per gram of dry product to be treated.

7. A method for extracting a dried Globularia alypum plant which comprises the following steps:
   (a) extracting under reflux for 15 minutes to 5 hours, 10 to 120 g of a plant material selected from the entire plants, the stems and the leaves of *Globularia alypum*, with 1 liter of water;
   (b) discarding the insoluble material and subjecting the solution to a lyophilisation;
   (c) subjecting the lyophilised product thus obtained to an extraction at 15°-25° C. for 2 to 4 hours, with a solvent selected from the group comprising methanol, ethanol and their mixtures with water, using 50 to 300 ml of solvent per gram of lyophilised product to be treated;
   (d) discarding the insoluble material and evaporating the solution to dryness under reduced pressure; and
   (e) dissolving the evaporation residue thus obtained into a solvent selected from the group comprising water, methanol, ethanol and mixtures thereof, subjecting the solution thus obtained to a column chromatography on a support suitable for molecular filtration, and recovering at the bottom of the column the first 3 volumes when pouring 10 volumes of solvent at the top of the column.

8. The method of claim 1 wherein the product of step (d) is purified by a process comprising molecular filtration by chromatography with a support which preferentially absorbs lower molecular weight substances to high molecular weight substances thereby recovering a product which is predominantly of high molecular weight.

* * * * *